US011001874B1

(12) United States Patent
Elaimi et al.

(10) Patent No.: US 11,001,874 B1
(45) Date of Patent: May 11, 2021

(54) SIMPLIFIED PCR METHOD FOR THE DETECTION OF COMMON NEUPLOIDES IN HUMAN REIMPLANTATION EMBRYOS

(71) Applicant: King Abdulaziz University, Jeddah (SA)

(72) Inventors: Aisha Elaimi, Jeddah (SA); Ashraf Dallol, Jeddah (SA); Adeel Chaudhary, Jeddah (SA); Adel Abuzinadah, Jeddah (SA); Muhammad Hussain Al-Qahtani, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 16/991,118

(22) Filed: Aug. 12, 2020

(51) Int. Cl.
*C12P 19/34* (2006.01)
*C12Q 1/6806* (2018.01)

(52) U.S. Cl.
CPC ...... *C12Q 1/6806* (2013.01); *C12Q 2531/113* (2013.01)

(58) Field of Classification Search
CPC .................................................... C12Q 1/6806
See application file for complete search history.

(56) References Cited

U.S. PATENT DOCUMENTS

| | | | | |
|---|---|---|---|---|
| 2008/0085836 A1* | 4/2008 | Kearns | C40B 40/08 | 506/2 |
| 2008/0176237 A1* | 7/2008 | Bhatt | C12Q 1/6883 | 435/6.12 |
| 2010/0015619 A1* | 1/2010 | Zhang | C12Q 1/6883 | 435/6.11 |
| 2010/0196897 A1* | 8/2010 | Manaresi | G01N 27/447 | 435/6.11 |

OTHER PUBLICATIONS

Girardet et al., Molecular Human Reproduction 9(2), 111-116 (2003). (Year: 2003).*

* cited by examiner

*Primary Examiner* — Kenneth R Horlick
(74) *Attorney, Agent, or Firm* — W&C IP

(57) ABSTRACT

Methods of detecting aneuploidy in in vitro fertilized embryos are provided. A unique set of STR markers that can be rapidly and accurately quantified by multiplex PCR at the single cell level are used to analyze and select euploid embryos in an in vitro fertilization (IVF) setting. The markers include D13S284, D13S141, D18S54, D18S70, D21S266, D21S1951 and AMXY and are used to detect abnormalities in chromosomes 13, 18, 21 and the XY chromosomes.

11 Claims, 12 Drawing Sheets

Specification includes a Sequence Listing.

```
                         SEQUENCE LISTING

<160> NUMBER OF SEQ ID NOS: 14

<210> SEQ ID NO 1
<211> LENGTH: 22
<212> TYPE: DNA
<213> ORGANISM: Artificial Sequence
<220> FEATURE:
<223> OTHER INFORMATION: Synthetic forward primer

<400> SEQUENCE: 1

ggccaaagat agatagcaag gt                                              22


<210> SEQ ID NO 2
<211> LENGTH: 20
<212> TYPE: DNA
<213> ORGANISM: Artificial Sequence
<220> FEATURE:
<223> OTHER INFORMATION: Synthetic reverse primer

<400> SEQUENCE: 2

gacagaacat cccaggctca                                                 20


<210> SEQ ID NO 3
<211> LENGTH: 20
<212> TYPE: DNA
<213> ORGANISM: Artificial Sequence
<220> FEATURE:
<223> OTHER INFORMATION: Synthetic forward primer

<400> SEQUENCE: 3

acgaagacaa tcaggaggca                                                 20


<210> SEQ ID NO 4
<211> LENGTH: 20
<212> TYPE: DNA
<213> ORGANISM: Artificial Sequence
<220> FEATURE:
<223> OTHER INFORMATION: Synthetic reverse primer

<400> SEQUENCE: 4

cccagtctta gtccccacac                                                 20


<210> SEQ ID NO 5
<211> LENGTH: 23
<212> TYPE: DNA
<213> ORGANISM: Artificial Sequence
<220> FEATURE:
<223> OTHER INFORMATION: Synthetic forward primer

<400> SEQUENCE: 5

tcaaacactt ctgcagacta tga                                             23
```

<210> SEQ ID NO 6
<211> LENGTH: 20
<212> TYPE: DNA
<213> ORGANISM: Artificial Sequence
<220> FEATURE:
<223> OTHER INFORMATION: Synthetic reverse primer

<400> SEQUENCE: 6
tatctggtgt gtggctgaca 20

<210> SEQ ID NO 7
<211> LENGTH: 20
<212> TYPE: DNA
<213> ORGANISM: Artificial Sequence
<220> FEATURE:
<223> OTHER INFORMATION: Synthetic forward primer

<400> SEQUENCE: 7
ggtgccccat agagagacaa 20

<210> SEQ ID NO 8
<211> LENGTH: 20
<212> TYPE: DNA
<213> ORGANISM: Artificial Sequence
<220> FEATURE:
<223> OTHER INFORMATION: Synthetic reverse primer

<400> SEQUENCE: 8
gtcccaaccc ctgagctaat 20

<210> SEQ ID NO 9
<211> LENGTH: 19
<212> TYPE: DNA
<213> ORGANISM: Artificial Sequence
<220> FEATURE:
<223> OTHER INFORMATION: Synthetic forward primer

<400> SEQUENCE: 9
aaactctcca gccacccct 19

<210> SEQ ID NO 10
<211> LENGTH: 23
<212> TYPE: DNA
<213> ORGANISM: Artificial Sequence
<220> FEATURE:
<223> OTHER INFORMATION: Synthetic reverse primer

<400> SEQUENCE: 10
tgaagaaagg caaatgaaga cct 23

<210> SEQ ID NO 11
<211> LENGTH: 20
<212> TYPE: DNA
<213> ORGANISM: Artificial Sequence
<220> FEATURE:
<223> OTHER INFORMATION: Synthetic forward primer

<400> SEQUENCE: 11
gagagggcgg ggacaaatat 20

<210> SEQ ID NO 12
<211> LENGTH: 21
<212> TYPE: DNA
<213> ORGANISM: Artificial Sequence
<220> FEATURE:
<223> OTHER INFORMATION: Synthetic reverse primer

```
<400> SEQUENCE: 12

agccattcca gccaaaatct g                                          21


<210> SEQ ID NO 13
<211> LENGTH: 20
<212> TYPE: DNA
<213> ORGANISM: Artificial Sequence
<220> FEATURE:
<223> OTHER INFORMATION: Synthetic forward primer

<400> SEQUENCE: 13

ccctgggctc tgtaaagaat                                            20


<210> SEQ ID NO 14
<211> LENGTH: 21
<212> TYPE: DNA
<213> ORGANISM: Artificial Sequence
<220> FEATURE:
<223> OTHER INFORMATION: Synthetic reverse primer

<400> SEQUENCE: 14

atcagagctt aaactgggaa g                                          21
```

SIMPLIFIED PCR METHOD FOR THE DETECTION OF COMMON NEUPLOIDES IN HUMAN REIMPLANTATION EMBRYOS

SEQUENCE LISTING

This application includes as the Sequence Listing the complete contents of the accompanying text file "Sequence.txt", created Aug. 5, 2020, containing 3,051 bytes, hereby incorporated by reference.

BACKGROUND OF THE INVENTION

Field of the Invention

The invention generally relates to improved methods of detecting aneuploidy and euploidy in in vitro fertilized embryos prior to implantation. In particular, the invention provides a unique set of STR markers that can be rapidly and accurately quantified by multiplex PCR at the single cell level to assist in the analysis and selection of embryos in an in vitro fertilization (IVF) setting.

Description of Related Art

Aneuploidy is a deviation from the normal number of chromosomes in which there is an extra or a missing copy of a chromosome (trisomy or monosomy) or chromosome set (triploidy). Non-disjunction, premature separation of sister chromatids and anaphase lagging are the mechanisms responsible for aneuploidy. Aneuploidy is the most widespread type of chromosomal abnormality and is directly proportional to advanced maternal age. Aneuploidy is considered to be a primary cause of miscarriage and implantation failure. The most commonly seen numerical abnormality in preimplantation embryos is trisomy, especially for the acrocentric chromosomes and sex chromosomes, although it can affect all human chromosomes. Most surviving embryos with numerical chromosomal abnormalities are those with Down syndrome (trisomy 21), Edward syndrome (trisomy 18), Patau syndrome (trisomy 13) and those with aneuploidies in sex chromosomes (monosomy X; i.e. Turner syndrome).

Currently there are several tests for aneuploidy at multiple levels. Commercial non-invasive prenatal testing which relies on screening for trisomies in fetal DNA in the mother's blood is increasingly becoming the method of choice for many expectant mothers. However, this test relies on next generation sequencing and to perform it, a lengthy validation procedure is required from the testing laboratory. At the pre-implantation level, e.g. during IVF procedures, genetic screening is commonly performed using next generation sequencing which adds extra layers of cost to the already expensive procedure.

A simple, quick and affordable test is needed for aneuploidy screening, e.g. to address the need for the increasing demand from families who opt for late pregnancies due to socio-economic or other reasons.

SUMMARY OF THE INVENTION

Provided herein are methods of detecting genetic abnormalities in in vitro fertilized embryos prior to implantation. The methods are advantageously based on analyses which are conducted at the level of single cell samples (biopsies) obtained from embryos. Thus, the embryos remain viable after sampling. In order to achieve this level of sensitivity, particular STR markers have been selected and tested. When amplified using e.g. low-cost single-tube multiplex PCR, the STR markers give detectable, accurate results at the single cell level within a short period of time (e.g. hours). The methods thus permit the rapid, pre-implant identification of embryos which have genetic abnormalities (e.g. various aneuploidies such as trisomies) and/or alternatively permit the identification of embryos which have do not have genetic abnormalities (the embryos are euploid), so that the latter can be selected for implantation. Aneuploid embryos are not selected and may be destroyed. The simple, straightforward and rapid design of the methods permits ready integration into an IVF setting as part of a standard and simplified PGS workflow, where short working time frames are crucial. Kits comprising means for detecting the STR markers are also provided.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

It is an object of this invention to provide a method of conducting in vitro fertilization in a human female, comprising obtaining a biopsy sample from at least one candidate embryo; determining the ploidy of each candidate embryo by amplifying, by multiplex polymerase chain reaction (PCR), at least three short tandem repeat (STR) markers selected from the group consisting of D13S284, D13S141, D18S54, D18S70, D21S266, D21S1951 and AMXY; implanting in the human female at least one embryo that is identified as euploid in the determining step. In some aspect, all of D13S284, D13S141, D18S54, D18S70, D21S266, D21S1951 and AMXY are amplified. In some aspect, the biopsy sample is a single cell. In other aspects, the at least one candidate embryo is obtained by in vitro fertilization of an ovum from the human female. In further aspects, the human female is at least 35 years old. In additional aspects, the step of determining takes 8 hours or less. In yet further aspects, the ploidy of chromosome 13, chromosome 18, chromosome 21 and the X chromosome is determined. And in additional aspect, the ploidy is determined without performing whole genome amplification (WGA).

Also provided is a kit comprising primers for PCR multiplex amplifying short tandem repeat (STR) markers D13S284, D13S141, D18S54, D18S70, D21S266, D21S1951 and AMXY.

DETAILED DESCRIPTION

Figure 1:
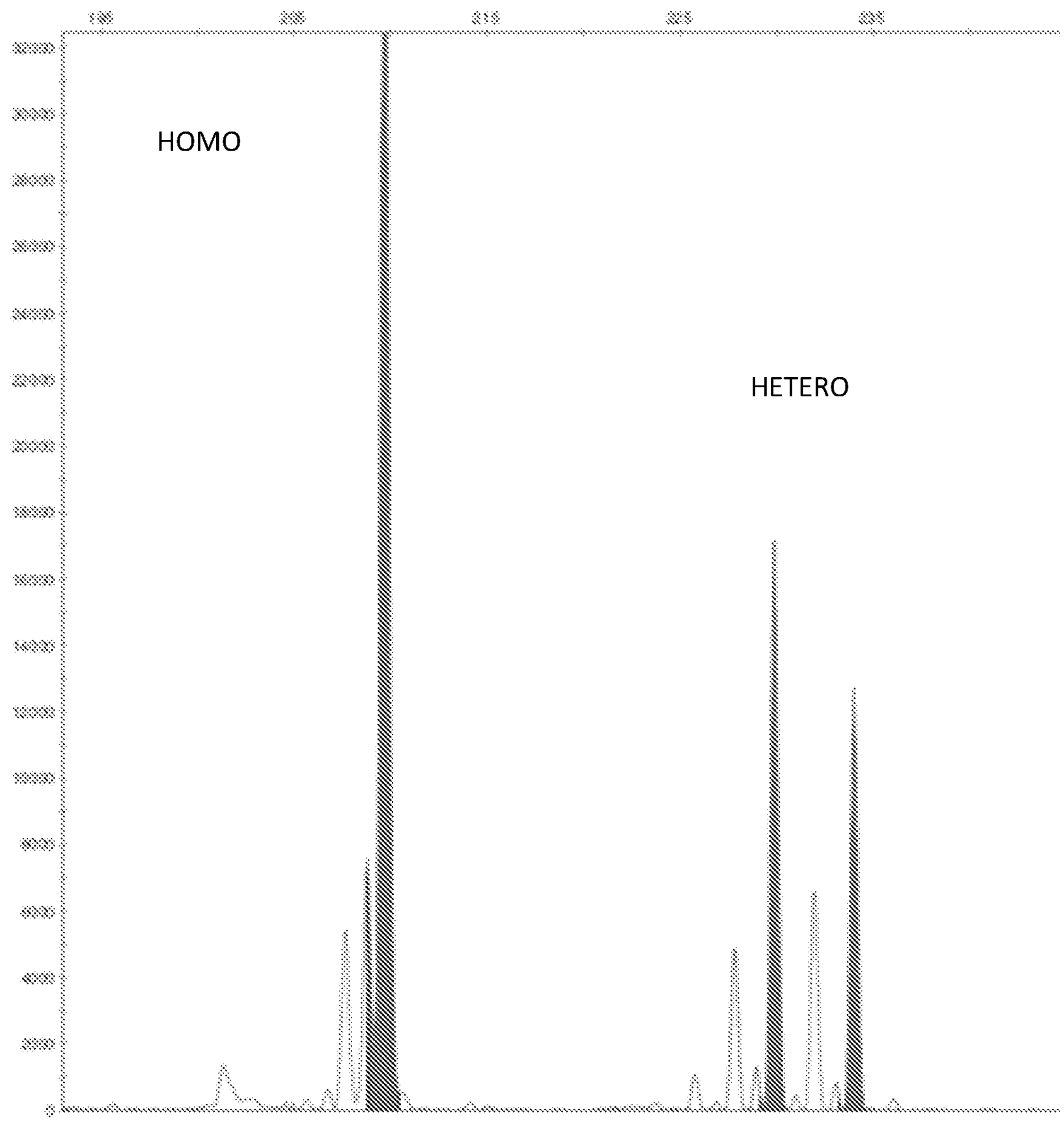
FIG. 1. Electrophotogram for chromosome 18 marker (D18S70). Left: Normal Homozygous for the marker, Right: Normal Heterozygous for the same marker (diallelic with 1:1 ratio).

Methods and kits for aneuploidy screening are provided. The methods and kits are based on multiplex polymerase chain reaction (PCR) amplification of target areas in the genome at the single cell level of sensitivity. PCR primers that target short tandem repeats (STRs) in human chromosomes 13, 18, 21 are used, as well as primers that detect the AMELX/Y gene (which is polymorphic on the X and Y chromosomes). The targeted markers include D13S284, D13S141, D18S54, D18S70, D21S266, D21S1951 and AMXY. Fluorescent labelling of the primers permits detection of the PCR products at a single base pair resolution. This approach advantageously uses standard and relatively inexpensive PCR reagents and instrumentation and requires a maximum of e.g. 8 hours from sampling to reporting. The analysis is performed directly on DNA from preimplantation samples (e.g. embryo biopsy samples) and eliminates the need for pre-analytical whole genome amplification (WGA). Since the methods do not require expensive and technically demanding hardware or specialty staff training, the cost of the assays is low and increases the affordability of aneuploidy screening.

Methods

Provided herein are methods of determining the ploidy of cells in a sample. Ploidy is determined e.g. by amplifying, by polymerase chain reaction (PCR), at least one, two, three or all four of chromosome 13, chromosome 18, chromosome 21 and AMXY. The short tandem repeat (STR) markers that are detected include the informative markers D13S284, D13S141, D18S54, D18S70, D21S266, D21S1951 and AMXY. Amplification determines the number of copies of a chromosome with which a marker pair is associated, e.g. markers D13S284 and D13S141 are associated with chromosome 13; markers D18S54 and D18S70 are associated with chromosome 18; markers D21S266, and D21S1951 are associated with chromosome 18; and the AMXY marker is associated with the amelogenin gene on the X and Y chromosomes. Thus, methods for determining, detecting or measuring the number of copies of chromosomes 13, 18, 21 and the amelogenin gene are provided.

Samples which are used to conduct the methods may be any suitable sample from any suitable source. Generally, the sample comprises DNA from an embryo or fetus, and usually comprises at least one cell from the embryo or fetus, although the analysis of nucleic acids such as DNA is also encompassed. Examples include but are not limited to: biopsy samples of at least one cell obtained directly from an embryo (which may be a frozen embryo) or fetus; polar body 1 and polar body 2 from the oocyte; blastomere (single cell) from cleavage stage embryos (day 3-4); trophectoderm biopsy (4-6 cells) of blastocyst (day 5 embryo); cells, nucleic acids or tissues obtained from transcervical of trans-abdominal Chorionic Villus Sampling (CVS); non-invasive cell-free fetal DNA-based screening e.g. cell-free fetal DNA (cffDNA) from maternal plasma; buccal swaps for maternal/paternal profiling In preferred aspects, the sample is at least one cell from an in vitro fertilized embryo that is a candidate for implantation. Candidate embryos may be obtained by fertilizing an ovum from a female in vitro. The ovum may be from the female who is to undergo implantation or may be from a female donor. Similarly, the ovum may be fertilized using sperm from a known male partner of the female or from a male donor.

In some aspects, the analyses are conducted in conjunction with a clinical in vitro fertilization procedure and the methods are used to select embryos suitable for implantation in the procedure, e.g. euploid embryos. Several fertilized embryos (e.g. at least about 10 or more) may be selected as candidate embryos, i.e. embryos that will be tested. Alternatively, candidate embryos may be tested one at a time until a euploid embryo is identified. The invention thus also encompasses methods of identifying euploid embryos.

Those of skill in the art will recognize that the methods and STR markers disclosed herein can be used e.g. to identify euploid embryos. However, the methods are not restricted to the analysis of embryos. Fetal ploidy may also be tested as may the ploidy of e.g. infants, children, and adults. Many subjects can benefit from the knowledge obtained from the rapid sensitive tests disclosed herein.

To conduct the methods, genomic DNA is obtained (isolated and purified or partially purified) from the sample by any of the method that are well-known in the art, and selected markers in the DNA are detected using a suitable technique. In some aspects, detection is via amplification, e.g. polymerase chain reaction (PCR) amplification. In some aspects, the PCR reaction is a multiplex PCR reaction, although singleplex reactions and isothermal amplification are also encompassed.

PCR amplification involves the use of primers, in particular, primers that flank the unique polymorphic STRs disclosed herein. Exemplary primers are shown in the Examples below and one or more of them may be used, but the practice of the invention is in no way limited to the use of those particular primers. Any primers which uniquely amplify the selected STRs and give a detectable signal may be used, e.g. primers that are further up- or downstream in the flanking regions of the STRs. Alternatively, primers with at least about 95% identity to those disclosed herein may be used, e.g. at least about 95, 96, 97, 98 or 99% identity. Combinations of one or more of the primers disclosed herein with other primers may also be used.

Further discussion of PCR amplification is provided, for example, in US patent application 20040137452, the complete contents of which is hereby incorporated by reference in entirety.

The primers are generally labelled with a detectable label to facilitate detection and quantification of the resulting amplicons. Examples of suitable detectable labels include but are not limited to: a magnetic label, a fluorescent moiety, an enzyme, a chemiluminescent probe, a metal particle, a non-metal colloidal particle, a polymeric dye particle, a pigment molecule, a pigment particle, an electrochemically active species, semiconductor nanocrystal or other nanoparticles including quantum dots or gold particles, fluorophores, quantum dots, or radioactive labels. Protein labels include green fluorescent protein (GFP) and variants thereof (e.g., cyan fluorescent protein and yellow fluorescent protein); and luminescent proteins such as luciferase, as described below. Radioactive labels include without limitation radioisotopes (radionuclides), such as $^{3}H$, $^{11}C$, $^{14}C$, $^{18}F$, $^{32}P$, $^{35}S$, $^{64}Cu$, $^{68}Ga$, $^{86}Y$, $^{99}Tc$, $^{111}In$, $^{123}I$, $^{124}I$, $^{125}I$, $^{131}I$, $^{133}Xe$, $^{177}Lu$, $^{211}At$, or $^{213}Bi$. Generally, the labels are fluorescent labels which include without limitation a rare earth chelate (e.g., europium chelate), rhodamine; fluorescein types including without limitation FITC, 5-carboxyfluorescein, 6-carboxy fluorescein; a rhodamine type including without limitation TAMRA; dansyl; Lissamine; cyanines; phycoerythrins; Texas Red; Cy3, Cy5, dapoxyl, NBD, Cascade Yellow, dansyl, PyMPO, pyrene, 7-diethylaminocoumarin-3-carboxylic acid and other coumarin derivatives, Marina Blue™, Pacific Blue™, Cascade Blue™, 2-anthracenesulfonyl, PyMPO, 3,4,9,10-perylene-tetracarboxylic acid, 2,7-difluorofluorescein (Oregon Green™488-X), 5-carboxyfluorescein, Texas Red™-X, Alexa Fluor 430, 5-carboxytetramethylrhodamine (5-TAMRA), 6-carboxytetramethylrhodamine (6-TAMRA), BODIPY FL, bimane, and Alexa Fluor 350, 405, 488, 500, 514, 532, 546, 555, 568, 594, 610, 633, 647, 660, 680, 700, and 750, and derivatives thereof, among many others. See, e.g., "The Handbook-A Guide to Fluorescent Probes and Labeling Technologies," Tenth Edition, available on the internet at probes (dot) invitrogen (dot) corn/handbook. The fluorescent label can be one or more of FAM, dRHO, 5-FAM, 6FAM, dR6G, JOE, HEX, VIC, TET, dTAMRA, TAMRA, NED, dROX, PET, BHQ, Gold540 and LIZ.

The results of the amplification procedure, i.e. the production of amplicons, may be analyzed by any suitable technology, but this is generally done e.g. using a DNA sequencer. The relative amounts of amplification products can be quantitated according to the label used, e.g. fluorescent dye. When the results are displayed graphically, the peak height on the output from the sequence analyzer can be used to quantitate the amount of amplification product present for each DNA marker. Generally, for example, in reaching a diagnosis of trisomy, the ratios of the peaks obtained for each amplification product are compared. Samples from euploid samples generally have either two STR allelic products with an ideal quantitative ratio of 1:1 or could be homozygous with two alleles of the same size (one peak but twice the size of a single allele). In contrast, samples from trisomic patients show either three different alleles with quantitative dose ratios of 1:1:1 (trisomic tri-allelic), or two PCR products with a ratio of 2:1 (trisomic di-allelic). However, it is possible for a trisomic sample to have three similarly sized STR alleles and so represent a single PCR product indistinguishable from a homozygote normal individual. In such circumstances, a diagnosis might not be possible. Efforts to avoid this problem include the use of a non-polymorphic marker as a control. The amelogenin gene exists as two copies, one on the X-chromosome (AMELX) and one on the Y-chromosome (AMELY). The two copies are almost identical with a small difference in length. For AMXY, using the exemplary primers disclosed herein, for a euploid female embryo, only one X-specific product of AMXY is detected (one peak representing the identical two alleles on the X-chromosome) and in a euploid male embryo both X and Y products of AMXY are detected. Further, in euploidy, the products are present in a 1:1 ratio. Deviations from this ratio indicate aneuploidy of some type.

However, to account for experimental margins of error, the present invention permits a diagnosis of a normal chromosomal complement with a peak ratio in the range of from about 1:1 to 1.4:1 for a particular STR marker. A diagnosis of di-allelic trisomy (diplozygous trisomy) can be made when the peak ratio is above about 1.6:1. These ratio values help to avoid false negative results.

Performance of the disclosed methods may take about 12, 11, 10, 9, 8, 7, or 6 hours or less, including decimal fractions of hours between those values. In advantageous aspects, the practice of the methods takes about 8 hours or less per sample, starting from when a sample, e.g. a single cell, is obtained for analysis but prior to isolation of the DNA.

After selection of at least one euploid embryo based on the analysis described above, the at least one euploid embryo is implanted in a female patient, i.e. a human female who is undergoing IVF. The woman may be undergoing IVF for any or a variety of reasons, e.g. fallopian tube damage or blockage, ovulation disorders, endometriosis, uterine fibroids, previous tubal sterilization or removal, impaired sperm production or function of a partner, unexplained infertility, a genetic disorder which could predispose a child to an unwanted disease or condition, past fertility preservation for cancer or other health conditions, or the woman may be a gestational carrier who carries the embryo for another, e.g. a women who does not have a functional uterus or for whom pregnancy poses a serious health risk.

Implantation is conducted by a skilled medical practitioner, such as a physician who specializes in IVF, according to techniques that are known in the art. Briefly, embryo transfer usually takes place two to five days after egg retrieval and fertilization via insertion of a catheter into the vagina, through the cervix and into the uterus. A syringe containing one or more embryos suspended in a small amount of fluid is attached to the end of the catheter and using the syringe, the doctor places the embryo or embryos into the uterus. If successful, an embryo will implant in the lining of the uterus about six to 10 days after egg retrieval.

Kit

Also provided herein is a kit of parts comprising at least one multiplex of labelled primers for carrying out a method of the present invention as described above. Suitably such kits can include at least one set of labelled primers for the STR markers to be amplified, polymerase buffer solution in which a DNA polymerase can extend the primers in the presence of DNA polymerase, and deoxynucleoside triphosphates. The labelled primers may include fluorescent labels as described elsewhere herein, and the DNA polymerase may be Taq DNA polymerase.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms “a”, “an”, and “the” include plural referents unless the context clearly dictates otherwise. It is further noted that the claims may be drafted to exclude any optional element. As such, this statement is intended to serve as support for the recitation in the claims of such exclusive terminology as “solely,” “only” and the like in connection with the recitation of claim elements, or use of a “negative” limitations, such as “wherein [a particular feature or element] is absent”, or “except for [a particular feature or element]”, or “wherein [a particular feature or element] is not present (included, etc.) . . . ”.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLES

Example 1

Primer Design

The invention herein involves the use of chromosome-specific targeting oligonucleotide primers that amplify polymorphic loci in a test (candidate) population, e.g. of embryos. To this end, a detailed homology search was performed in which candidate STR markers were screened for potential annealing and amplification. The search yielded 2 STRs per chromosome to which oligonucleotide primers were designed (See Table 1). In order to achieve visualization and to resolve the STR size, the forward primer for each STR marker was labelled with a different fluorescence moiety (Table 1). The selection of the fluorescent labels ensures the ability to perform the reaction in a multiplex fashion.

TABLE 1

Exemplary primers

| Markers | Chromosome band | Label of forward primer | Sequence of primers | SEQ ID NO: |
|---|---|---|---|---|
| D13S284-F | 13q14.3 | 6FAM- | GGCCAAAGATAGATAGCAAGGT (forward) | 1 |
| D13S284-R | | | GACAGAACATCCCAGGCTCA (reverse) | 2 |
| D13S141-F | 13q12.11 | TAMRA- | ACGAAGACAATCAGGAGGCA (forward) | 3 |
| D13S141-R | | | CCCAGTCTTAGTCCCCACAC (reverse) | 4 |
| D18S54-F | 18p11.31 | 6FAM- | TCAAACACTTCTGCAGACTATGA (forward) | 5 |
| D18S54-R | | | TATCTGGTGTGTGGCTGACA (reverse) | 6 |
| D18S70-F | 18q23 | HEX- | GGTGCCCCATAGAGAGACAA (forward) | 7 |
| D18S70-R | | | GTCCCAACCCCTGAGCTAAT (reverse) | 8 |
| D21S266-F | 21q22.3 | TAMRA- | AAACTCTCCAGCCACCCCT (forward) | 9 |
| D21S266-R | | | TGAAGAAAGGCAAATGAAGACCT (forward) | 10 |
| D21S1951-F | 21q11.2 | HEX- | GAGAGGGCGGGGACAAATAT (forward) | 11 |
| D21S1951-R | | | AGCCATTCCAGCCAAAATCTG (reverse) | 12 |
| AMXY-F | Xp22.2/Yp1 1.2 | 6FAM- | CCCTGGGCTCTGTAAAGAAT (forward) | 13 |
| AMXY-R | | | ATCAGAGCTTAAACTGGGAAG (reverse) | 14 |

Polymerase Chain Reaction (PCR)

The polymerase chain reaction (PCR) was performed either in singleplex or in a multiplex fashion using the exemplary primers listed in Table 1 in equimolar amounts. The reaction master mix used was the Multiplex PCR kit from Qiagen, which was used according to the manufacturer's instructions. The PCR condition were: a melting cycle of 95° C. for 15 minutes followed by 10 cycles of 96° C. for 30 seconds, 60° C. for 90 seconds, and 72° C. for 90 seconds. This cycle is repeated for an additional 30 cycles with the melting temperature reduced to 94° C. An additional cycle of 72° C. for 10 minutes was included at the end to ensure complete extension of the PCR products.

Fragment (PCR product) analysis was performed on the Genetic analyzer 3500 (ThermoFisher). The PCR products (1 μl) were loaded with a mix of 12 μl formamide and 0.3 μl of a ROX™ 500 molecular size standard and analyzed on the instrument with a POP-7™ and 50 cm sequencing capillary. The results were visualized using GeneMapper version 5 software from ThermoFisher.

Sample Preparation

A QIAamp® DNA Mini Kit from Qiagen was used for DNA extraction from peripheral blood samples, amniotic fluid samples and Chorionic Villus Sampling (CVS) samples according to the manufacturer's instruction. Blastomeres biopsied from day 3 embryos were incubated at −80° C. with freshly prepared ALB buffer (200 mM NaOH and 50 mM dithiothreitol) for 45 minutes to 1 hour followed by incubation at 65° C. for 10 minutes. 2.5 μl of 200 mM Tricine was added in order to neutralize the NaOH prior to using directly in the PCR step.

Analysis

Data was collected in the form of the number of peaks and their heights representative of heterozygosity and the fluorescence intensity emitted from the tag used in the reaction. In samples from normal individuals it is expected that each marker will have 2 peaks with a ratio of 1:1 indicating that the STR marker is present in 2 alleles (i.e. the marker is heterozygous and present in two copies, one from each chromosome). The STRs used in this invention are highly polymorphic with a high heterozygosity index. Therefore, when a single peak is present the marker is rendered uninformative and indicates homozygosity or monosomy. Trisomies are indicated when 3 equal sized peaks with a ratio of 1:1:1 or two peaks with a ratio of 2:1 are detected.

The choice of the STR markers relies on their existence in a polymorphic state in the majority of samples. To this end, up to 12 samples from healthy volunteers were screened using the STR markers detailed in Table 1. The results show that all markers exhibited a high heterozygosity index (No. of samples with heterozygous state/Total number of samples; see Table 2).

TABLE 2

Heterozygosity index determination and peak ratios for the STR markers described in this invention

| Marker | Heterozygozity Index | PEAK AREAS (RATIO) Mean | SD | Range |
|---|---|---|---|---|
| D13S284 | 1.00 | 1.45 | 0.17 | 1.2-1.7 |
| D13S141 | 0.75 | 1.09 | 0.12 | 1-1.32 |
| D18S54 | 0.92 | 1.45 | 0.23 | 1-1.6 |
| D18S70 | 0.92 | 1.35 | 0.2 | 1-1.7 |
| D21S266 | 0.92 | 1.12 | 0.17 | 1-1.4 |
| D21S1951 | 0.92 | 1.14 | 0.26 | 1-1.7 |

Figure 2:
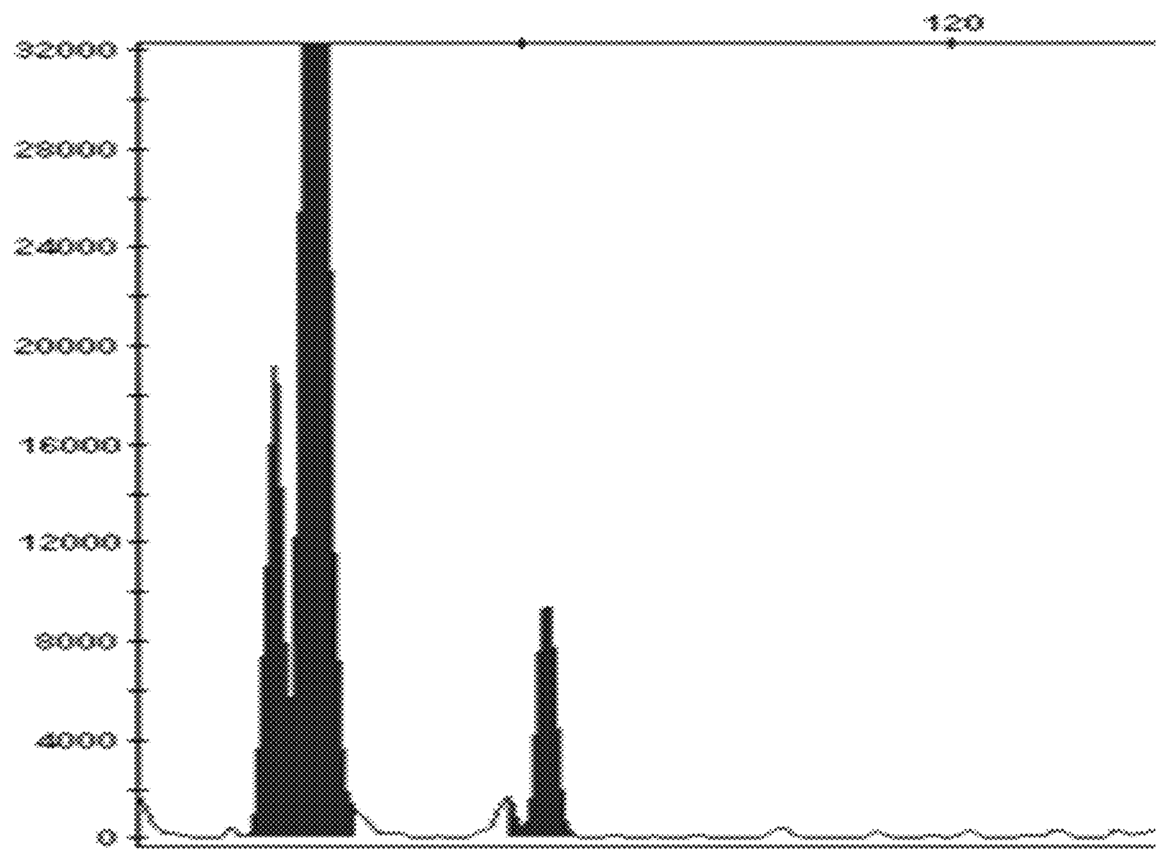
FIG. 2. Electrophotogram for chromosome X marker for single cell sample (blastomere) showing three copies with a monoallelic pattern with a 3:1 ratio.
Figure 3:
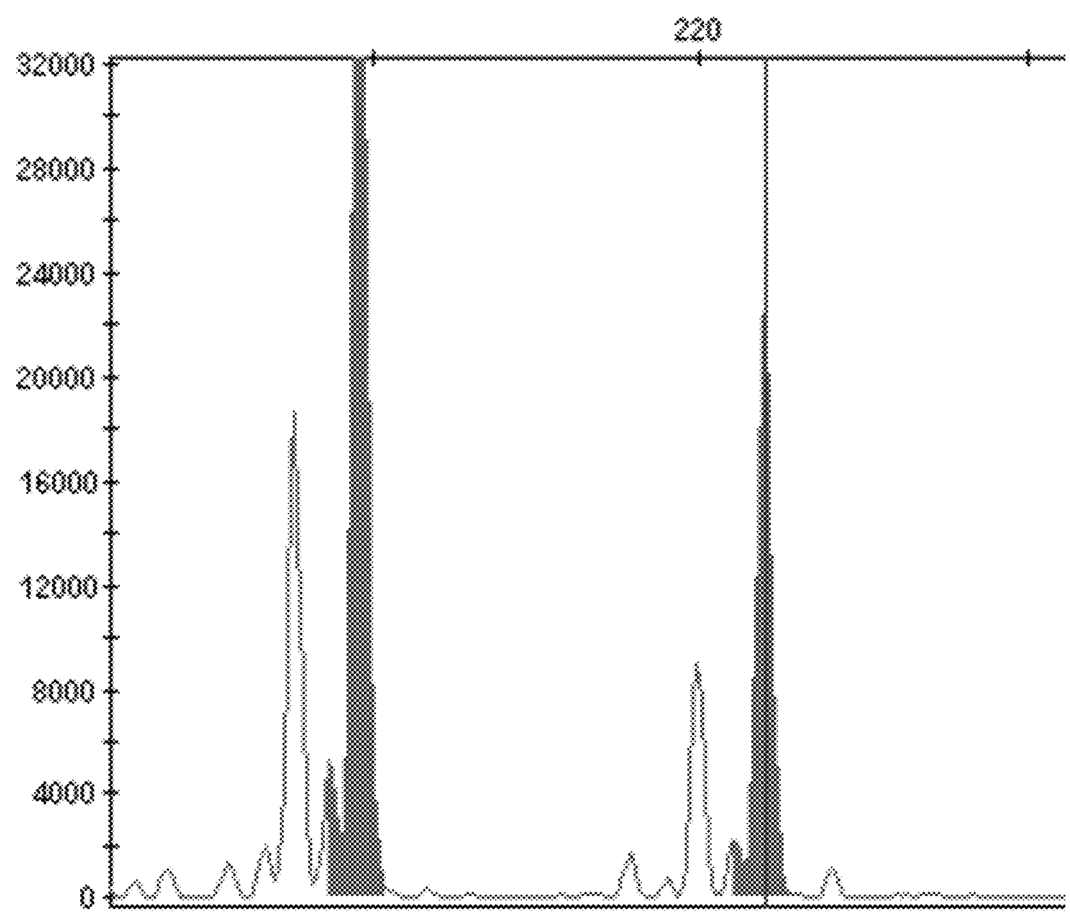
FIG. 3. Electrophotogram for chromosome 21 (D21S1951). A single cell sample (blastomere) showing trisomy 21 in a diallelic pattern with a 2:1 ratio.
Figure 4:
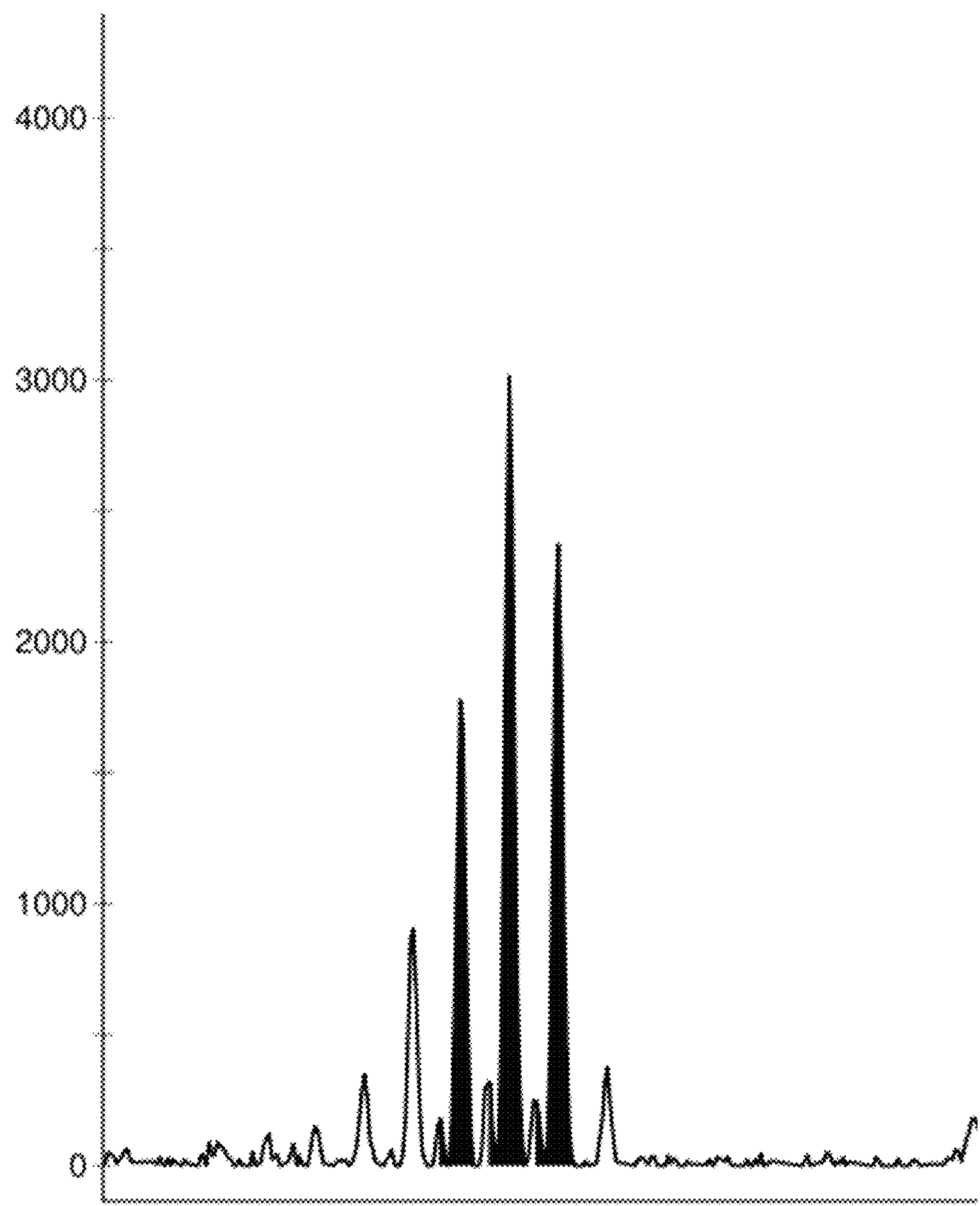
FIG. 4. Electrophotogram for chromosome 21 (D21S266). A single cell sample (blastomere) with a triallelic pattern of trisomy 21 (ratio 1:1:1).
Figure 5A:
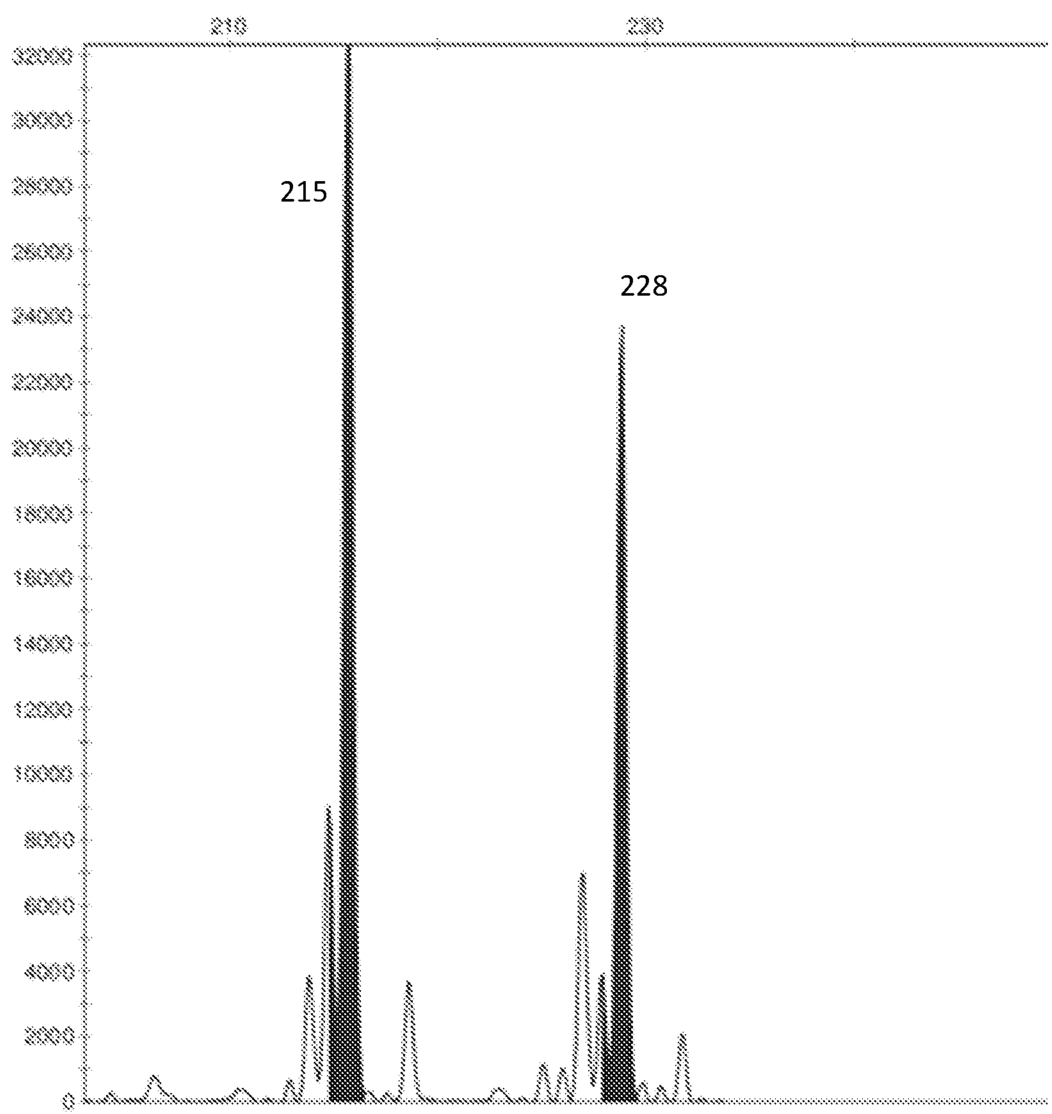
FIG. 5A-D. Electrophotogram for an amniotic fluid sample. A and B, the mother and father diallelic normal patterns, respectively. C, the amniotic fluid results showing a copy of the mother's alleles (i.e. contamination is clear). D, the new sample after retesting showing the alleles of the mother and father.
Figure 5B:
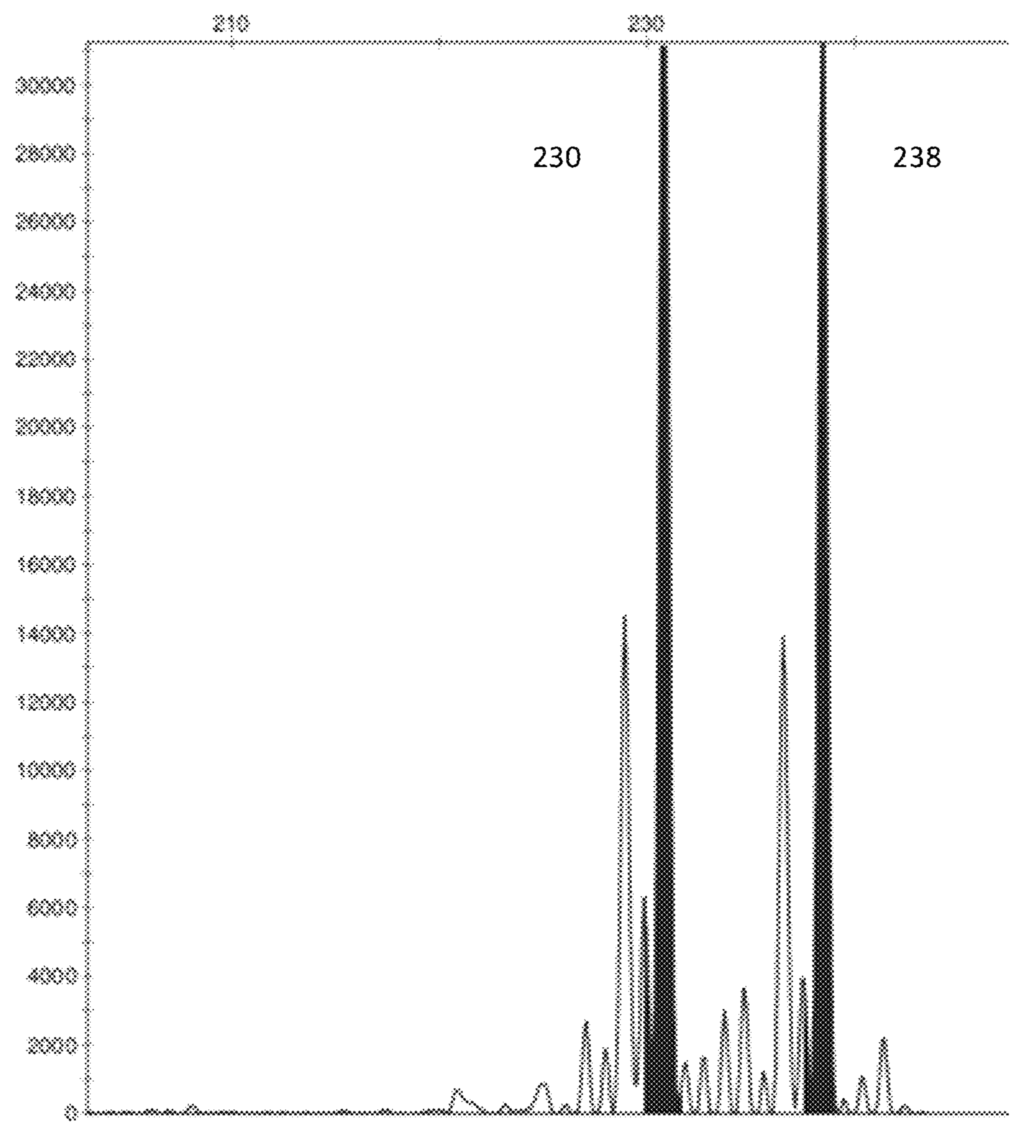
Figure 5C:
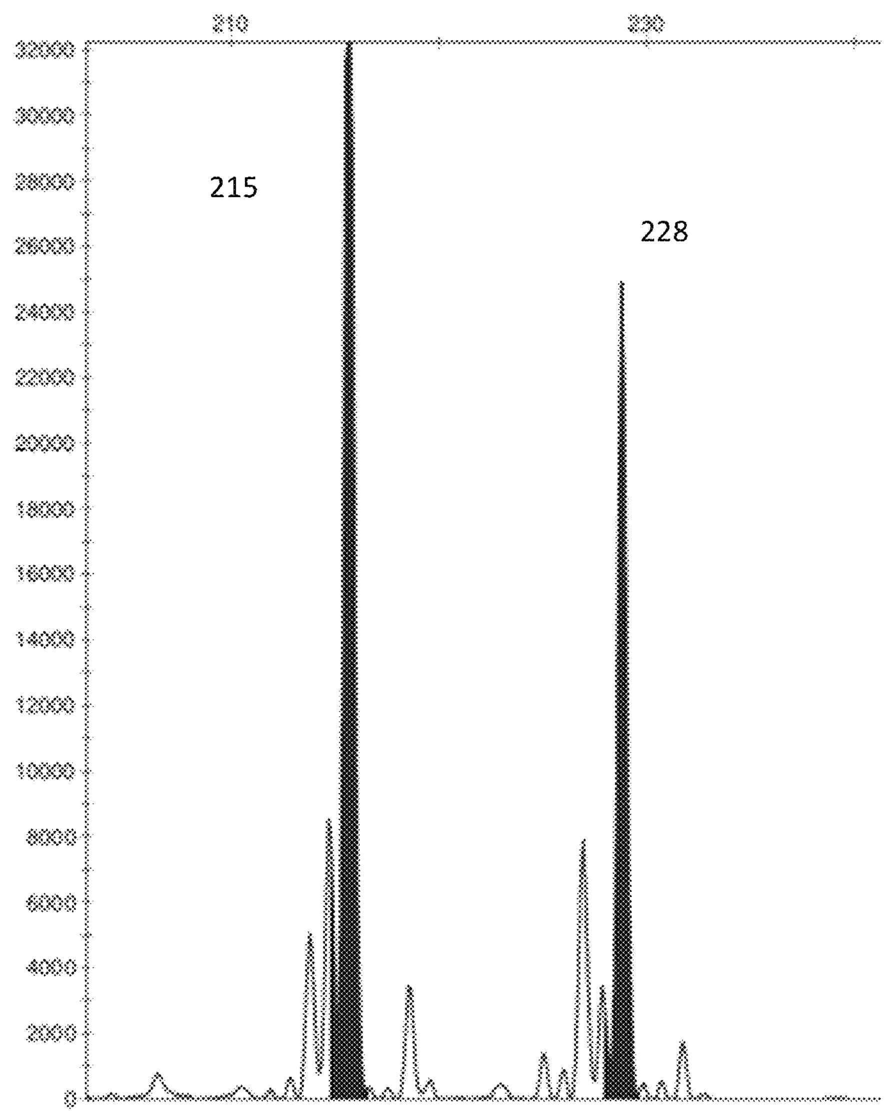
Figure 5D:
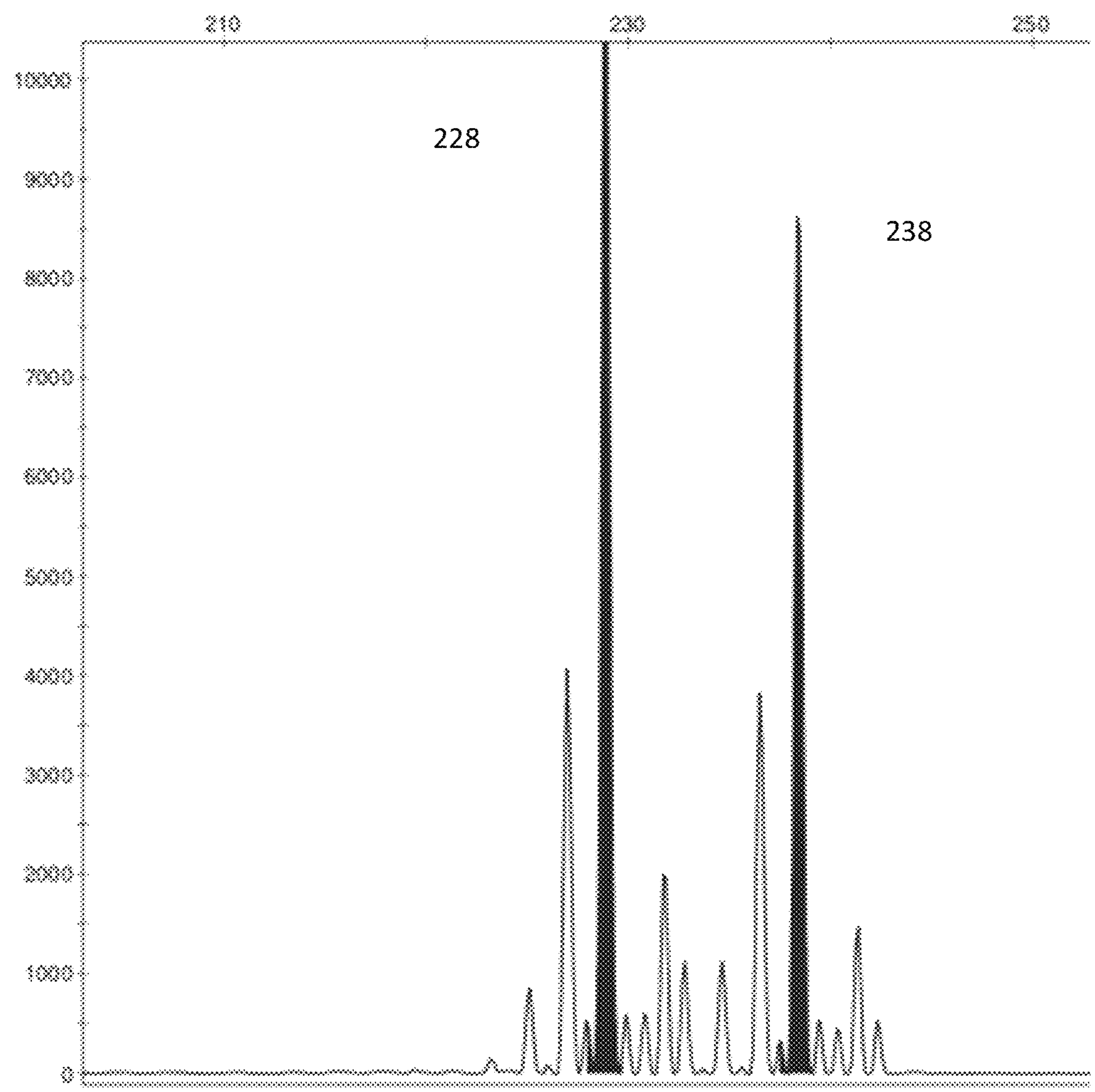

STR markers should demonstrate specificity and sensitivity for their target chromosomes. To this end, the PCR products were analyzed on a DNA Analyzer and visualized using the GeneMapper™ v5 software. As shown in FIG. 1, the peaks are clearly defined with minimal background and the markers demonstrate sensitivity sufficient to distinguish chromosome copy number (FIGS. 2-4). FIG. 5 demonstrates the utility of this assay for re-testing for its ease of use and affordability.

Figure 6:
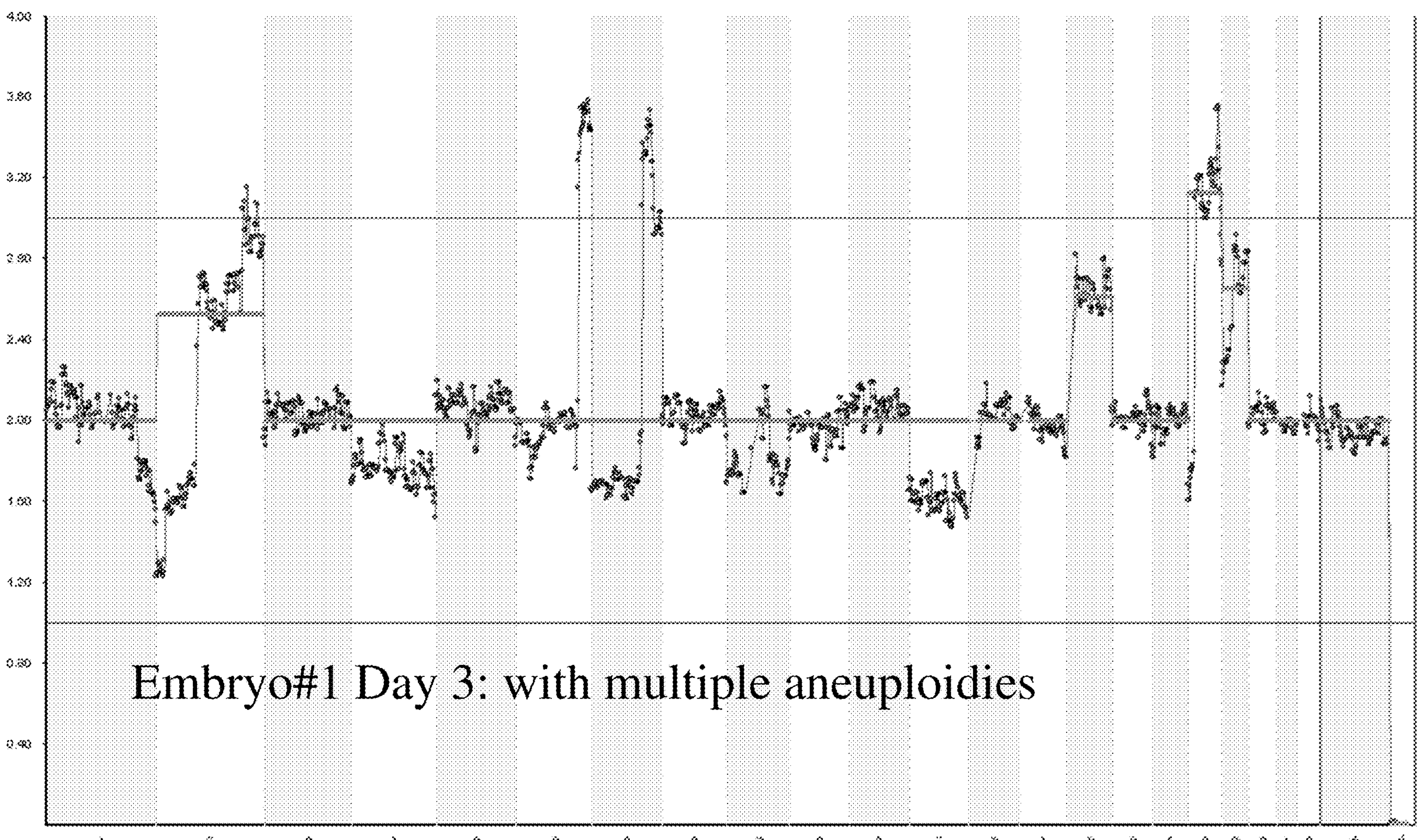
FIG. 6. Self-repair as detected using the NGS-based method.
Figure 6:
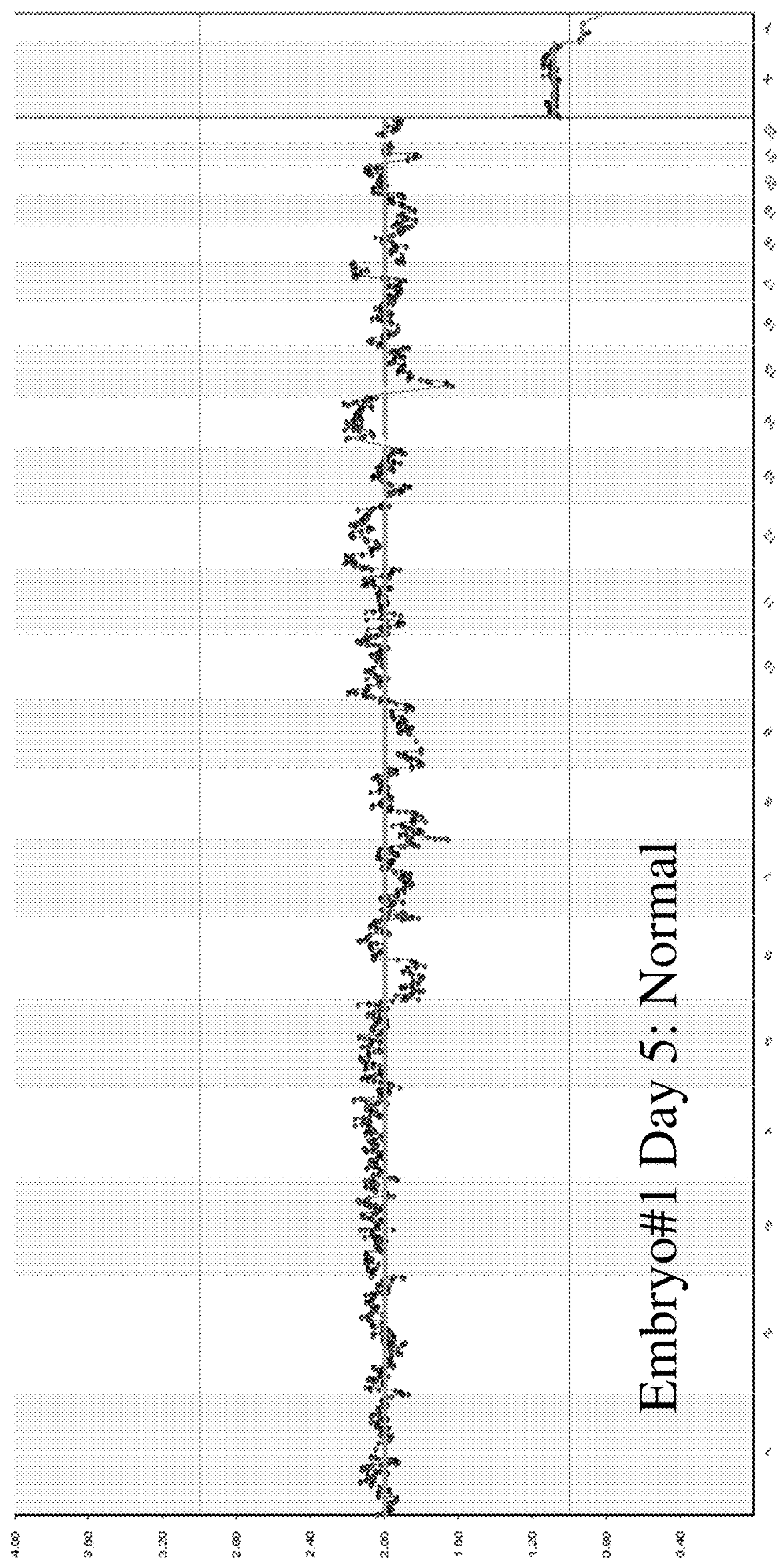
Figure 6:
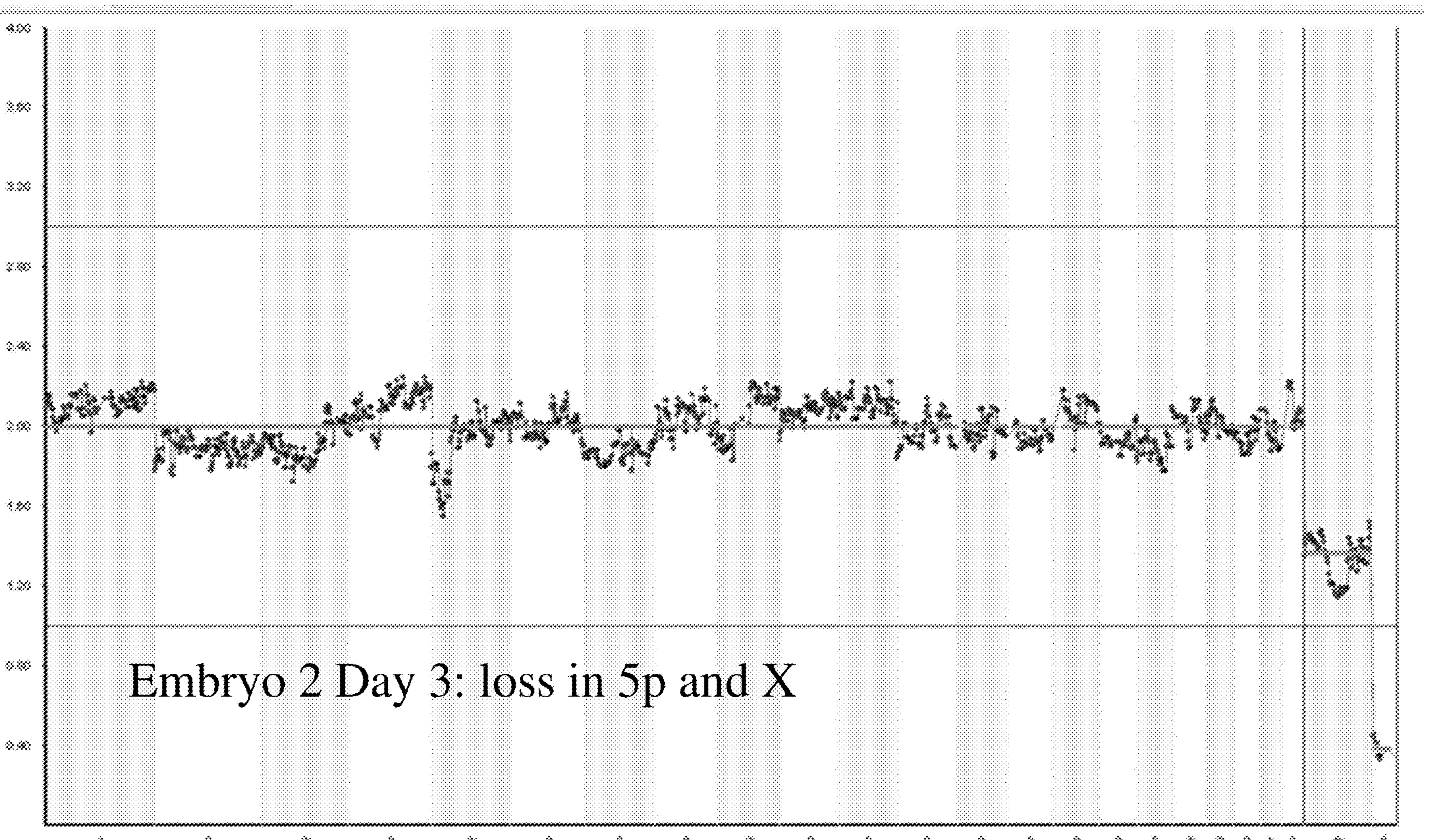
Figure 6:
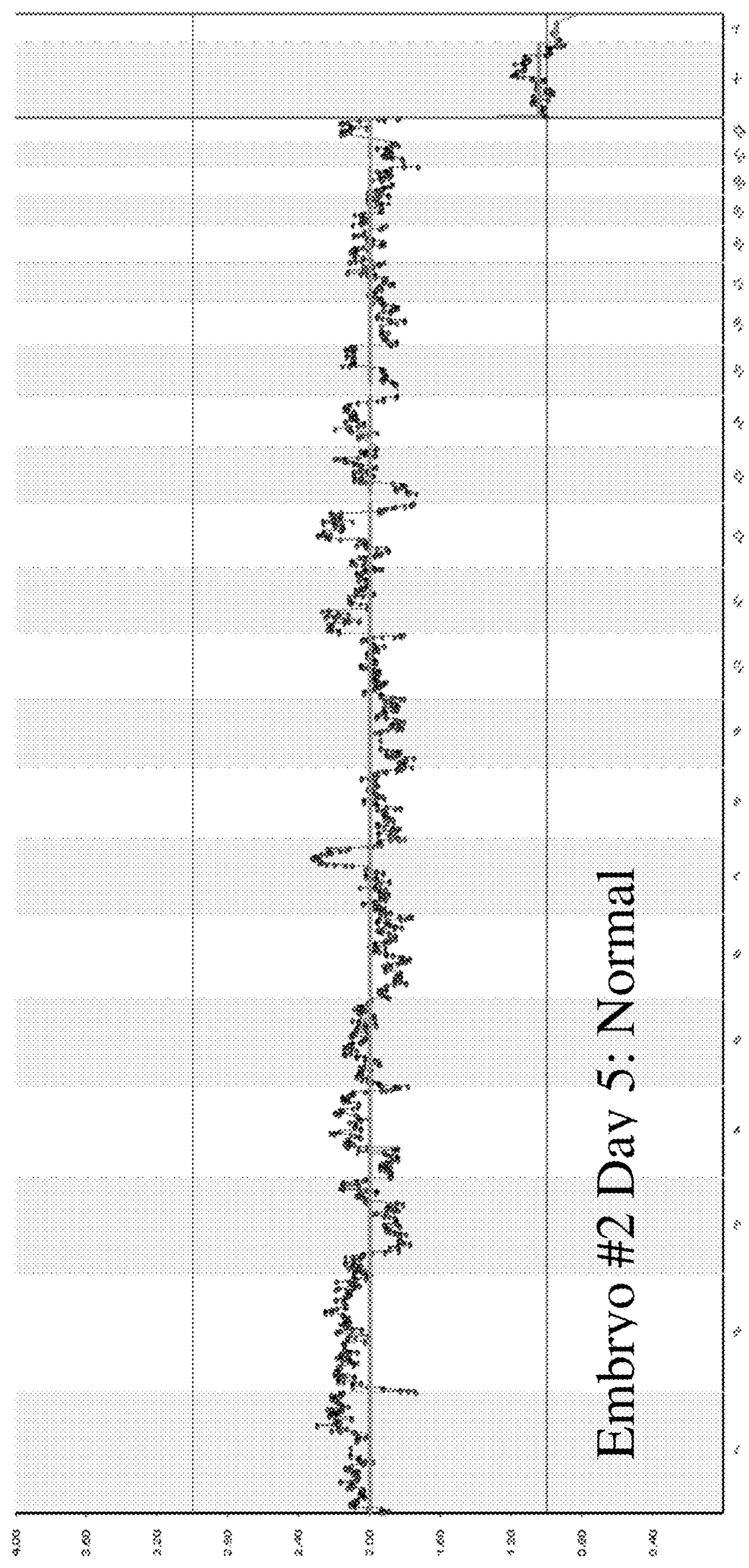

The method is designed for aneuploidy screening without the need for NGS-based methods that often lead to false positive diagnoses and does not account for self-repair. As shown in FIG. 6, NGS-based methods show discrepancies caused by differences in days of sampling before and after self-repair in the same embryo.

REFERENCES

[1] M. Viotti, Preimplantation genetic testing for chromosomal abnormalities: Aneuploidy, mosaicism, and structural rearrangements, Genes (Basel). 11 (2020). doi: 10.3390/genes11060602.

[2] H. Hall, P. Hunt, and T. Hassold, Meiosis and sex chromosome aneuploidy: how meiotic errors cause aneuploidy; how aneuploidy causes meiotic errors, Curr. Opin. Genet. Dev. 16 (2006) 323-329. doi:10.1016/j.gde.2006.04.011.

[3] J. M. Kemper, B. J. Vollenhoven, and A. J. Talmor, Preimplantation Genetic Testing for Aneuploidy: A Review, Obstet. Gynecol. Surv. 74 (2019) 727-737. doi: 10.1097/OGX.0000000000000737.

[4] E. Fragouli, M. Katz-Jaffe, S. Alfarawati, J. Stevens, P. Colls, N. N. Goodall, S. Tormasi, C. Gutierrez-Mateo, R. Prates, W. B. Schoolcraft, S. Munne, and D. Wells, Comprehensive chromosome screening of polar bodies and blastocysts from couples experiencing repeated implantation failure, Fertil. Steril. 94 (2010) 875-887. doi:10.1016/j.fertnstert.2009.04.053.

[5] A. Mantzouratou, A. Mania, E. Fragouli, L. Xanthopoulou, S. Tashkandi, K. Fordham, D. M. Ranieri, A. Doshi, S. Nuttall, J. C. Harper, P. Serhal, and J. D. A. Delhanty, Variable aneuploidy mechanisms in embryos from couples with poor reproductive histories undergoing preimplantation genetic screening, Hum. Reprod. 22 (2007) 1844-1853. doi:10.1093/humrep/dem102.

[6] K. D. Sanders, and D. K. Griffin, Chromosomal Preimplantation Genetic Diagnosis: 25 Years and Counting, J. Fetal Med. 4 (2017) 51-56. doi:10.1007/s40556-017-0123-5.

[7] S. Munné, A. Lee, Z. Rosenwaks, J. Grifo, and J. Cohen, Fertilization and early embryology: Diagnosis of major chromosome aneuploidies in human preimplantation embryos, Hum. Reprod. 8 (1993) 2185-2191. doi: 10.1093/oxfordjournals.humrep.a138001.

[8] A. R. Thornhill, C. E. deDie-Smulders, J. P. Geraedts, J. C. Harper, G. L. Harton, S. A. Lavery, C. Moutou, M. D. Robinson, A. G. Schmutzler, P. N. Scriven, K. D. Sermon, and L. Wilton, ESHRE PGD Consortium Best practice guidelines for clinical preimplantation genetic diagnosis (PGD) and preimplantation genetic screening (PGS),' Hum. Reprod. 20 (2005) 35-48. doi:10.1093/humrep/deh579.

[9] S. Munné, J. Fischer, A. Warner, S. Chen, C. Zouves, and J. Cohen, Preimplantation genetic diagnosis significantly reduces pregnancy loss in infertile couples: A multicenter study, Fertil. Steril. 85 (2006) 326-332. doi:10.1016/j.fertnstert.2005.10.014.

[10] W. B. Schoolcraft, E. Fragouli, J. Stevens, S. Munne, M. G. Katz-Jaffe, and D. Wells, Clinical application of comprehensive chromosomal screening at the blastocyst stage, Fertil. Steril. 94 (2010) 1700-1706. doi:10.1016/j.fertnstert.2009.10.015.

[11] I. Findlay, T. Tóth, P. Matthews, T. Marton, P. Quirke, and Z. Papp, Rapid trisomy diagnosis (21, 18, and 13) using fluorescent PCR and short tandem repeats: Applications for prenatal diagnosis and preimplantation genetic diagnosis, in: J. Assist. Reprod. Genet., 1998: pp. 266-275. doi:10.1023/A:1022536309381.

[12] B. Pertl, S. Kopp, P. M. Kroisel, M. Hausler, J. Sherlock, R. Winter, and M. Adinolfi, Quantitative fluorescence polymerase chain reaction for the rapid prenatal detection of common aneuploidies and fetal sex, Am. J. Obstet. Gynecol. 177 (1997) 899-906. doi:10.1016/S0002-9378(97)70292-8.

[13] W. Schmidt, J. Jenderny, K. Hecher, B.-J. Hackelöer, S. Kerber, L. Kochhan, and K. R. Held, Detection of aneuploidy in chromosomes X, Y, 13, 18 and 21 by QF-PCR in 662 selected pregnancies at risk, Mol. Hum. Reprod. 6 (2000) 855-860. doi:10.1093/molehr/6.9.855.

[14] M. Adinolfi, J. Sherlock, and B. Pertl, Rapid detection of selected aneuploidies by quantitative fluorescent PCR, BioEssays. 17 (1995) 661-664. doi:10.1002/bies.950170712.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

This work was funded by the Deanship of Scientific Research (DSR), King Abdulaziz University, Jeddah, Saudi Arabia, under grant No. (IFPRC-010-290-2020). The authors, therefore, acknowledge with thanks DSR technical and financial support.

We claim:

1. A method of conducting in vitro fertilization in a human female, comprising obtaining a biopsy sample from at least one in vitro fertilized candidate embryo prior to implantation;

determining the ploidy in each in vitro fertilized candidate embryo by amplifying, by multiplex polymerase chain reaction (PCR), the short tandem repeat (STR) markers D13S284, D13S141, D18S54, D18S70, D21S266, D21S1951 and AMXY;

implanting in the human female at least one in vitro fertilized embryo that is identified as euploid in the determining step.

2. The method of claim 1, wherein the biopsy sample is a single cell.

3. The method of claim 1, wherein the at least one in vitro fertilized candidate embryo is obtained by in vitro fertilization of an ovum from the human female.

4. The method of claim 1, wherein the human female is at least 35 years old.

5. The method of claim 1, wherein the step of determining takes 8 hours or less.

6. The method of claim 1, wherein the ploidy of chromosome 13, chromosome 18, chromosome 21 and the X chromosome is determined.

7. The method of claim 1, wherein the ploidy is determined without performing whole genome amplification (WGA).

8. A kit comprising primers for PCR multiplex amplifying short tandem repeat (STR) markers D13S284, D13S141, D18S54, D18S70, D21S266, D21S1951 and AMXY, wherein each primer is labeled with a detectable label.

9. The kit of claim 8, wherein the detectable label is a magnetic label, a fluorescent label, an enzyme, a chemiluminescent probe, a metal particle, a non-metal colloidal particle, a polymeric dye particle, a pigment molecule, a pigment particle, an electrochemically active species, a semiconductor nanocrystal, quantum dots, gold particles, a radioactive label or a protein label.

10. The method of claim 1, wherein the STR markers have a heterozygosity index from 0.75 to 1.0.

11. A reaction mixture comprising primers specific for amplifying the short tandem repeat (STR) markers D13S284, D13S141, D18S54, D18S70, D21S266, D21S1951 and AMXY, wherein the primers are present at equimolar concentrations, and wherein each primer is labeled with a detectable label.

* * * * *